United States Patent [19]

Wacker

[11] 4,293,355
[45] Oct. 6, 1981

[54] METHOD FOR ULTRASONICALLY WELDING PLASTICIZED THERMOPLASTIC POLYMERIC FOAM WARES

[75] Inventor: Albert R. Wacker, Zionsville, Ind.

[73] Assignee: Cabot Corporation, Kokomo, Ind.

[21] Appl. No.: 73,928

[22] Filed: Sep. 10, 1979

Related U.S. Application Data

[62] Division of Ser. No. 900,982, Apr. 28, 1978, Pat. No. 4,193,396.

[51] Int. Cl.³ .................. A61F 11/02; B23K 19/04
[52] U.S. Cl. .................. 156/73.2; 128/152; 156/73.1; 264/23
[58] Field of Search ............ 156/73.1, 73.2, 580.1, 156/580.2, 78; 128/152; 181/135, DIG. 1

[56] References Cited

U.S. PATENT DOCUMENTS

| | | | |
|---|---|---|---|
| Re. 29,487 | 12/1977 | Gardner, Jr. | 128/152 |
| 2,230,738 | 2/1941 | Baum | 128/152 |
| 3,625,787 | 12/1971 | Radl et al. | 156/73.2 |
| 3,837,950 | 9/1974 | Reimels | 156/73.2 |

*Primary Examiner*—Michael G. Wityshyn
*Attorney, Agent, or Firm*—Jack Schuman; Robert F. Dropkin

[57] ABSTRACT

Disclosed herein is a tethered earplug construction comprising a pair of plasticized thermoplastic foam earplugs tethered together by one or more flexible plasticized thermoplastic cord elements. Attachment of the cord element to the earplug is achieved by ultrasonic welding.

6 Claims, 3 Drawing Figures

METHOD FOR ULTRASONICALLY WELDING PLASTICIZED THERMOPLASTIC POLYMERIC FOAM WARES

CROSS-REFERENCE

This application is a division of my U.S. patent application Ser. No. 900,982, filed Apr. 28, 1978, now U.S. Pat. No. 4,193,396 issued Mar. 18, 1980.

BACKGROUND OF THE INVENTION

The present invention relates broadly to hearing protectors of the earplug type and is more specifically concerned with earplugs composed of plasticized thermoplastic foam materials.

Plasticized thermoplastic foam earplugs are known from such literature as British Pat. No. 733,542, to Gustav Hultgren, filed Oct. 16, 1953 and U.S. Pat. No. Re. 29,487, to Gardner, Jr., issued Dec. 16, 1977. Hultgren discloses earplugs formed of a soft spongy material which preferably consists of a softened vinyl chloride polymer or copolymer. The noise damping effects of the earplugs are disclosed to be controllable through control of the density and pore size of the spongy material of construction. Gardner, Jr. discloses earplugs composed of a resilient plasticized polymeric foam, such as polyvinyl chloride or polyurethane. The polymeric foam material of construction contains a sufficiently high concentration of organic plasticizer as to provide said material with certain rate of recovery and equilibrium pressure properties and, by virtue of this combination of properties, the earplugs of Gardner, Jr., upon compression thereof, are readily insertable into human ear canals whereupon they expand to provide comfortable and uniform sealing of the canals and act as highly competent sound barriers.

For use in certain environments it is often desirable to provide earplug type hearing protectors with suitable means to prevent their loss should they work loose or otherwise be dislodged. For instance, this is an important feature to provide for workers in the food processing industry wherein all due care must be exercised in preventing foreign matter from entering the foodstuff products. Likewise, those who work at substantial elevations or heights, such as iron and steel workers, are also desirably provided with bearing protector wares which are not susceptible of accidental loss.

It is known to provide earplug constructions comprising a pair of earplugs which are tethered together in spaced relation by means of a cord element which may be secured to the user's person or clothing. However, earplug constructions of this type have, heretofore, been essentially limited to those earplugs composed of unfoamed polymeric or elastomeric materials. Unfortunately, these unfoamed earplugs generally do not confer as uniformly competent hearing protection as do plasticized polymeric foam earplugs such as taught in the hereinbefore-mentioned Gardner, Jr. patent. It has been proposed to thermally weld a flexible thermoplastic cord to earplugs composed of plasticized thermoplastic foam materials. However, this has not heretofore been successfully accomplished on a practical assembly line basis to the knowledge of the present applicant. Indeed, the art has generally recognized that ultrasonic sealing or welding of plasticized polyvinylchloride materials cannot normally be achieved. For instance, at page 1345 of Volume 3 of The Encyclopedia of PVC, edited by Leonard I. Nass, Marcel Dekker, Inc., New York, 1977 it is stated: "Ultrasonic sealing cannot be used with flexible or plasticized PVC. The high-frequency sonic vibrations are not effective in generating the heat of fusion in soft substances." It also appears that one aspect of the problem resides in the tendency of thermoplastic polymeric foam materials to rapidly collapse upon application of welding heat thereto, thereby to result in substantial distortion of the earplug and to result in an excessively weak weldment or union between the earplug and the thermoplastic cord element. In accordance with the present invention, however, this problem has been solved.

OBJECTS OF THE INVENTION

It is a principal object of the invention to provide a novel tethered earplug construction wherein a pair of earplugs composed of a plasticized thermoplastic polymeric foam material are tethered together by means of one or more flexible plasticized thermoplastic cords.

It is another object of the invention to provide a novel tethered earplug construction defining a necklace to be worn around the neck of the user.

It is another object of the invention to provide a method for thermally welding a flexible plasticized thermoplastic element to a plasticized thermoplastic polymeric foam ware such as to provide an adequately strong union while avoiding deleteriously extensive collapse of the cell structure of the polymeric foam ware.

Other objects and advantages of the invention will, in part, be obvious and will, in part, appear hereinafter.

SUMMARY OF THE INVENTION

In accordance with the invention, the tethered earplug construction comprises at least one cord element composed of a flexible plasticized thermoplastic material, the ends of which cord element(s) are ultrasonically welded to a pair of earplugs composed of a plasticized thermoplastic polymeric foam material.

The method of the invention comprises rigidly supporting that portion of a ware composed of a plasticized thermoplastic foam material to be involved in the weldment, applying an element composed of a flexible plasticized thermoplastic material against said supported portion of the foam material by application of an ultrasonic transducer thereto and by spacing of said transducer from said rigid support as to define a gap within which said element is biased against said supported portion of said foam material, applying sufficient ultrasonic energy through said transducer for a sufficient period of time as to cause fluxing of the materials of both said element and said supported portion of said foam and cooling the resulting welded assembly to below fluxing temperature while maintaining it within the gap defined between said transducer and support.

THE DRAWING

DESCRIPTION OF THE PREFERRED EMBODIMENTS

Figure 1:
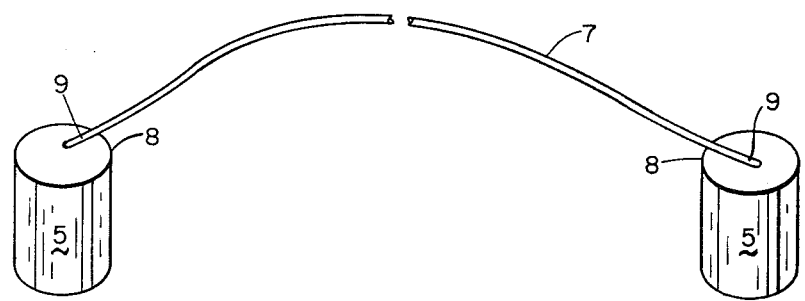
FIG. 1 is a schematic, diagrammatic perspective view of one embodiment of the tethered earplug construction of the invention.

Referring now to FIG. 1, the tethered earplug construction of the invention broadly comprises a pair of earplugs 5, each composed of a plasticized thermoplastic polymeric foam material and at least one cord element 7 composed of a flexible plasticized thermoplastic polymer. Each end 9 of cord 7 is ultrasonically welded to one or the other of the earplugs 5. Generally speaking, the earplugs 5 can be composed of any suitable plasticized thermoplastic polymer foam. Accordingly, foamed polymers of ethylene, propylene, vinyl chloride, vinyl acetate, diisocyanate, cellulose acetate or isobutylene can all be generally employed. Generally preferred are vinyl chloride homopolymers and copolymers comprising at least 85 percent by weight of vinyl chloride and up to 15 percent by weight of other monomers such as vinylidene chloride; vinyl esters of carboxylic acids, e.g., vinyl acetate, vinyl propionate, vinyl butyrate and vinyl benzoate; esters of unsaturated acids, e.g., alkyl acrylates such as methyl acrylate, ethyl acrylate, propyl acrylate, butyl acrylate, allyl acrylate, and the corresponding esters of methacrylic acid; vinyl aromatic compounds, e.g., styrene, orthochlorostyrene, para-chlorostyrene, 2,5-dichlorostyrene, 2,4-dichlorostyrene para-ethylstyrene, vinyl naphthalene and $\alpha$-methyl styrene; dienes such as butadiene and chlorobutadiene; unsaturated amides such as acrylic acid amide and acrylic acid anilide; unsaturated nitriles such as acrylic acid nitrile; and esters of $\alpha,\beta$-unsaturated carboxylic acids, e.g., the methyl, ethyl, propyl, butyl, amyl, hexyl, heptyl, octyl, allyl, methallyl, and phenyl esters of maleic, crotonic and fumaric acids and the like. It is also much preferred that the earplugs 5 each be composed of a plasticized thermoplastic polymeric foam material containing a sufficient concentration of an organic plasticizer therein as to meet the teachings of U.S. Pat. No. Re. 29,487, mentioned previously. For further details relative to specific plasticized thermoplastic formulations and methods of fabrication of such earplugs reference may be had to said patent which is specifically incorporated herein by reference thereto.

Cord element 7 can be composed of substantially any flexible plasticized thermoplastic material. Preferably, the cord element 7 will be composed of an unfoamed plasticized thermoplastic polymer containing few, if any, vacuoles. Moreover, it will usually also be preferred that said cord element 7 be a single strand construction as opposed to braided or twisted multi-strand constructions. For purposes of ensuring compatibility it is generally also desirable that the thermoplastic polymer employed for the cord element of the invention be chemically similar to the polymer employed in the fabrication of the earplugs 5. For example, where the earplugs 5 are composed of a polymer or copolymer or mixture wherein the prevailing monomer is vinyl chloride, it will normally be desirable that the thermoplastic material from which the cord element is constructed also be composed predominantly of a vinyl chloride polymer. It is further desirable that the cord element 7 be flexible and limp in order that it tend to drape close to the body of the user and in order to mitigate against transmission of sound to the ear plug through said cord element. This can usually be provided by use of sufficient plasticizer in the composition thereof. Finally as regards the cord element 7, said element should, of course, be of sufficient strength as to accomplish its intended purpose of securing the earplugs to the wearer; however, it should not be so strong as to constitute a hazard to the wearer should it become entangled in machinery or other apparatus. This tailoring of strength of the cord element 7 can usually be readily accomplished by suitable formulation of the thermoplastic material of construction thereof and/or by selection of a suitable cross-sectional dimension thereof. The length of cord element 7 is subject to considerable variation and it is enough to say that said length should obviously be such as to sufficiently space the earplugs for use while providing enough slack to ensure the cord element to some convenient apparel of the wearer. On the other hand, the cord element 7 should not be so lengthy as to constitute a hazard or to interfere with the wearer's activities.

Figure 2:
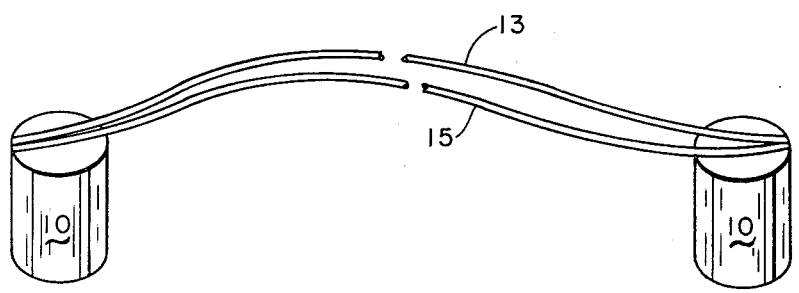
FIG. 2 is a schematic, diagrammatic perspective view of another embodiment of the tethered earplug construction of the invention wherein said construction defines a necklace.
Figure 3:
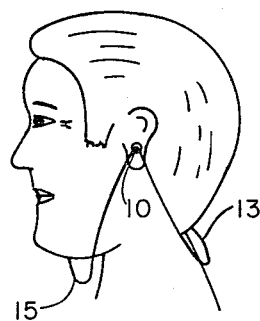
FIG. 3 is a schematic, diagrammatic side view disclosing one manner of use of the tethered earplug construction of FIG. 2.

As mentioned, it is intended that the cord element 7 be secured in any suitable fashion to the wearer. For instance, where safety hats are employed in the environment, a suitable clip may be employed to secure the cord element to the hat. Alternatively, the element 7 may be pinned or otherwise secured to other clothing worn by the user. In the embodiment of the construction of the invention shown in FIGS. 2 and 3, however, such additional measures for securing of the cord element 7 are not required. Referring now to said Figures, it will be seen that this construction comprises a pair of earplugs 10 tethered together by means of two cord elements 13 and 15, respectively, which may be of equal or different lengths. As shown more clearly in FIG. 3, this construction may be employed as a necklace whereby, upon insertion of the earplugs 10 into the ear canals, the cord element 15 is caused to hang to the front of the wearer while the cord element 13 is caused to hang behind the wearer's neck. Should one or both of the earplugs 10 be dislodged, they are secured against loss by this necklace arrangement.

An important aspect of the tethered earplug construction of the invention resides in the use of ultrasonic energy to weld the ends of the plasticized thermoplastic cord elements to the plasticized thermoplastic foam earplugs. Referring to FIG. 1 for illustrative purposes, this ultrasonic welding can be achieved by supporting a portion of sidewall 8 of plug 5 against a metallic anvil. End 9 of cord element 7 is placed against the end of earplug 5 and an ultrasonic transducer or "horn" is urged against said end 9 so as to define a gap within which the end 9 is biased firmly against the polymeric foam of the earplug. Desirably, the contacting surfaces of at least the supporting anvil will be knurled or otherwise textured so as to more securely capture the thermoplastic assemblage to be welded. The ultrasonic transducer is energized with sufficient power and for a sufficient duration such that the thermoplastic material of the end 9 of cord 7 is fluxed along with the foam material of the earplug 5. Ultrasonic frequencies of about 20 KHz, or greater, at power outputs of about 380 watts, mechanical, have been found to be suitable. The duration of application of the ultrasonic energy will normally be very short, typically on the order of about 0.3 second. Upon completion of the ultrasonic transducer operation, the welded assemblage is maintained within the gap between transducer and anvil until the resulting weldment has cooled to below the fluxing temperature thereof. Normally, the cooling period necessary will also be of relatively short duration under ambient temperature conditions.

The weldments produced by ultrasonic welding of the thermoplastic assemblages in accordance with the above disclosed methodology are characterized by their relative strength and by the fact that that portion of the plasticized thermoplastic foam material forming part thereof is not completely fluxed into a solid continuous state. This last is believed important since it indicates that a clearcut line of demarcation between thermoplastic foam material and weldment material is avoided, thus providing for more uniform distribution of whatever physical loads are subsequently applied to the weldment and avoiding undue stress concentrations therein.

Employing the ultrasonic welding technique of the invention tethered earplug constructions are readily fabricated utilizing earplugs composed of plasticized polyvinylchloride foams containing substantial concentrations of organic plasticizers and an extruded highly plasticized flexible single strand polyvinylchloride cord element having a diameter of about 0.060 inch. The bond strengths of such weldments are found to be typically within the range of about 2 to 2.5 pounds, which is entirely adequate for the purposes of the tethered earplug constructions of the invention.

Having thus described the invention, it will be apparent to those of ordinary skill in the art to make various changes and modifications in the embodiments of the invention specifically disclosed in the foregoing description and the drawing hereof. It is to be noted, therefore, that the concepts disclosed herein are intended to be limited only by the appended claims.

The embodiments of the invention in which an exclusive property or privilege is claimed are defined as follows:

1. A method for thermally welding an element composed of a flexible plasticized thermoplastic material to a ware composed of a plasticized thermoplastic polymeric foam which comprises:
   supporting the polymeric foam;
   bringing said element into abutting relationship with said foam;
   applying an ultrasonic transducer and spacing said transducer from said support so as to define a fixed gap therebetween within which said element is biased against said foam;
   energizing said transducer with sufficient power and for a sufficient period of time as to flux the plasticized thermoplastic materials of said element and said foam; and
   cooling the resulting weldment to below fluxing temperature, a portion of said foam forming a part of said weldment not being completely fluxed into a solid continuous state.

2. The method of claim 1 wherein said element and said ware are each comprised of a homopolymer or copolymer comprising at least 85 percent by weight of vinyl chloride.

3. The method of claim 1 wherein said transducer is energized at a frequency of at least about 20 KHz and at a mechanical power output of about 380 watts.

4. The method of claim 1 wherein the duration of energizing of said transducer is on the order of about 0.3 second.

5. The method of claim 1 wherein said element is a cord element and said ware is an earplug.

6. The method of claim 1 wherein the weldment is cooled to below fluxing temperature while maintaining the welded assemblage within said gap.

* * * * *